United States Patent
Kadri et al.

(10) Patent No.: US 11,138,347 B2
(45) Date of Patent: Oct. 5, 2021

(54) CLINIC PHYSICAL DESIGN AND LAYOUT

(71) Applicant: Kadri Medical Ltd., Windsor (CA)

(72) Inventors: Albert Kadri, Windsor (CA); Mohammed J. Ibrahim, Windsor (CA)

(73) Assignee: Kadri Medical Ltd., Windsor (CA)

( * ) Notice: Subject to any disclaimer, the term of this patent is extended or adjusted under 35 U.S.C. 154(b) by 0 days.

(21) Appl. No.: 16/751,832

(22) Filed: Jan. 24, 2020

(65) Prior Publication Data

US 2020/0159972 A1 May 21, 2020

Related U.S. Application Data

(63) Continuation-in-part of application No. 16/112,835, filed on Aug. 27, 2018.

(60) Provisional application No. 62/569,737, filed on Oct. 9, 2017, provisional application No. 62/796,347, filed on Jan. 24, 2019.

(51) Int. Cl.
  *G06F 30/13* (2020.01)
  *G06F 30/20* (2020.01)

(52) U.S. Cl.
  CPC .............. *G06F 30/13* (2020.01); *G06F 30/20* (2020.01)

(58) Field of Classification Search
  CPC .................................. G06F 30/13; G06F 30/20
  See application file for complete search history.

(56) References Cited

U.S. PATENT DOCUMENTS

| | | | |
|---|---|---|---|
| 4,259,816 A * | 4/1981 | Bergquist | E04H 3/04 52/236.1 |
| 5,748,907 A | 5/1998 | Crane | |
| 2003/0230031 A1 | 12/2003 | Lam | |
| 2004/0111290 A1 | 6/2004 | Crane | |
| 2008/0221919 A1* | 9/2008 | Cates | E04H 3/08 705/2 |
| 2013/0054271 A1 | 2/2013 | Langford | |
| 2015/0001923 A1 | 1/2015 | Felt | |
| 2015/0019238 A1 | 1/2015 | Felt | |

OTHER PUBLICATIONS

McGough, et al. "Redesigning Your Work Space to Support Team-Based Care", Fam Pract Manag. Mar.-Apr. 2013;20(2):20-24. (Year: 2013).*

McGough PM, Jaffy MB, Norris TE, Sheffield P, Shumway M. Redesigning your work space to support team-based care. Fam. Pract. Manag. Mar.-Apr. 2013; 20(2):20-4. PMID: 23547610. (Year: 2013).

* cited by examiner

*Primary Examiner* — Matthew Mikels
(74) *Attorney, Agent, or Firm* — The Dobrusin Law Firm, PC (57) ABSTRACT

A medical clinic layout including a waiting room, reception area, modular clinic pods, patient exam rooms, physician workspace, pharmacy, laboratory, urgent care, imaging . . . etc. optimizing the medical clinic layout's efficiency. These components are specifically fashioned to work synergistically to increase the efficiency of healthcare delivery and improve health outcomes, while also moving away from provider-centered care to patient-centered care.

4 Claims, 7 Drawing Sheets

CLINIC PHYSICAL DESIGN AND LAYOUT

CROSS REFERENCE TO RELATED APPLICATIONS

This application is a continuation-in-part application of U.S. application Ser. No. 16/112,835 filed on Aug. 27, 2018 which claims priority of U.S. provisional application Ser. No. 62/569,737 filed Oct. 9, 2017 and also claims priority and benefit to U.S. provisional application Ser. No. 62/796,347 filed on Jan. 24, 2019.

TECHNICAL FIELD

The present specification generally relates design for a medical clinic. More specifically, the present design and layout includes a novel layout to facilitate unidirectional patient flow through the clinic so as to enhance clinic efficiency, coordination of care between primary care physicians, specialist physicians, and essential services.

BACKGROUND

In the medical field, it is standard to have a primary care physician office fully separate and spaced apart from any specialist physician. As is standard, a patient will first visit a primary care physician and then, if required, be referred to a specialist. The patient must then make an appointment with that specific specialist, often many months later. If desired, the patient must then make a separate appointment with another specialist for a second opinion.

As a background, in one application of medicine, vascular healthcare is examined. Cardiovascular disease is a leading cause of death in North America and has become a public health epidemic. Cardiovascular disease and the associated risk factors are linked to an increased risk of morbidity and mortality and are also responsible for escalating healthcare costs. Traditionally, if a primary care physician thinks that a patient should be examined by a cardiologist, the patient is referred to a cardiologist and must make an appointment with the cardiologist's office, often at an entirely different location. When a second opinion is desired, as is often the case, the patient is again responsible for making an appointment. This system delays healthcare delivery to the patient, is time consuming, inconvenient and very costly. Separate EMRs (electronic medical records), and poor information sharing adds to the dysfunctional delivery of care. The current system is highly disjointed and inefficient for practitioners and patients alike.

Typically, a high-risk vascular patient must visit several different specialist physicians (cardiologist, endocrinologist, nephrologist, etc.), medical laboratories, imaging facilities, a pharmacy, and their primary care physician. Usually, each of these encounters occurs at different locations and together comprise basic healthcare. The clinical information from each of these separate encounters is not readily available to the individual healthcare providers and is almost always not available to the patient. This process results in the patient being less involved in their healthcare decisions. The patient is further burdened with the responsibility of coordinating multiple appointments (and time away from work) to manage their health.

Accordingly, improved approaches are needed within healthcare systems to address this epidemic and improve patient education, attendance, and adherence to strategies known to improve health outcomes while limiting financial burden. As such, a need exists in an improved medical clinic design, enhanced by an improved clinic layout suited to optimize the patient's time in clinic, healthcare involvement and overall health outcomes.

SUMMARY

The present specification provides for a building structure housing a medical facility, the building structure contained within a rectangular configuration, the building structure having two spaced apart building entrances, the building entrances positioned on opposed exterior walls, the building structure having at least two spaced apart building exits, the building exits positioned on opposed exterior walls, the building exits positioned on exterior walls separate from and perpendicular to said walls having said building entrances, an enclosed space defining a medical lab area positioned in one of the four corners of the building structure, an enclosed space defining a pharmacy area positioned in another of the four corners of the building structure, an enclosed space defining an urgent care area positioned in another of the four corners of the building structure, an enclosed space defining an imaging area positioned in the last of the four corners of the building structure, each of the medical lab, the pharmacy, the urgent care, and the imaging areas spaced apart from each other and a plurality of pods each having a plurality of exam rooms, each of the exam rooms having a dedicated first entrance/exits for patients and a dedicated second entrance/exit for care providers, the second dedicated entrance/exit for use only by care providers wherein a layout of the building structure facilitates efficient patient flow and optimizes efficiency in healthcare provider-patient interactions.

In some embodiments, at least two pods are provided of said plurality of pods wherein at least one primary care pod and at least one specialty care pod are provided. In other embodiments, the at least one primary care pod is spaced apart from the at least one specialty care pod. In other embodiments, each of the plurality of pods includes a hallway spacing apart two sets of exam rooms. This unique clinic layout also minimizes the area required to provide multidisciplinary and multispecialty healthcare.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, where like structure is indicated with like reference numerals and in which:

DETAILED DESCRIPTION

The present specification discloses a medical clinic layout including a waiting room, reception area, modular clinic pods, patient exam rooms, physician workspace, pharmacy, laboratory, urgent care, imaging . . . etc. along with corresponding flow arrows to illustrate the optimization of the medical clinic layout's efficiency. The present application includes a unique physical and operational design for a vascular health clinic, by way of example. It should be understood that the present clinic layout can apply to various different health specialties and practices and is not limited to vascular health. These components are specifically fashioned to work synergistically to increase the efficiency of healthcare delivery and improve health outcomes, while also moving away from provider-centered care to patient-centered care. The design also minimizes the area required to provide multidisciplinary and multispecialty healthcare.

The design of the present specification is configured to eliminate the fundamental problems, as previously described, with the current healthcare model. Patients will have access to their primary care physician, a select group of vascular health specialists, including cardiology, nephrology, endocrinology, neurology, and vascular surgery (available on-demand for 'quick' problem specific consultation), a medical laboratory, imaging, diagnostics, and pharmacy services, all at the same location, and in the same visit.

By implementing the below described design and utilizing the corresponding computer program and companion mobile device application (as described in the parent), healthcare providers will be able to increase the efficiency and quality of healthcare delivery, facilitate and simplify coordination of care, enhance patient involvement in healthcare decisions and measure and improve health outcomes in patients with vascular disease through clinical evidence-based strategies. By implementing this complete design, a new gold standard of healthcare will be achieved.

Figure 1:
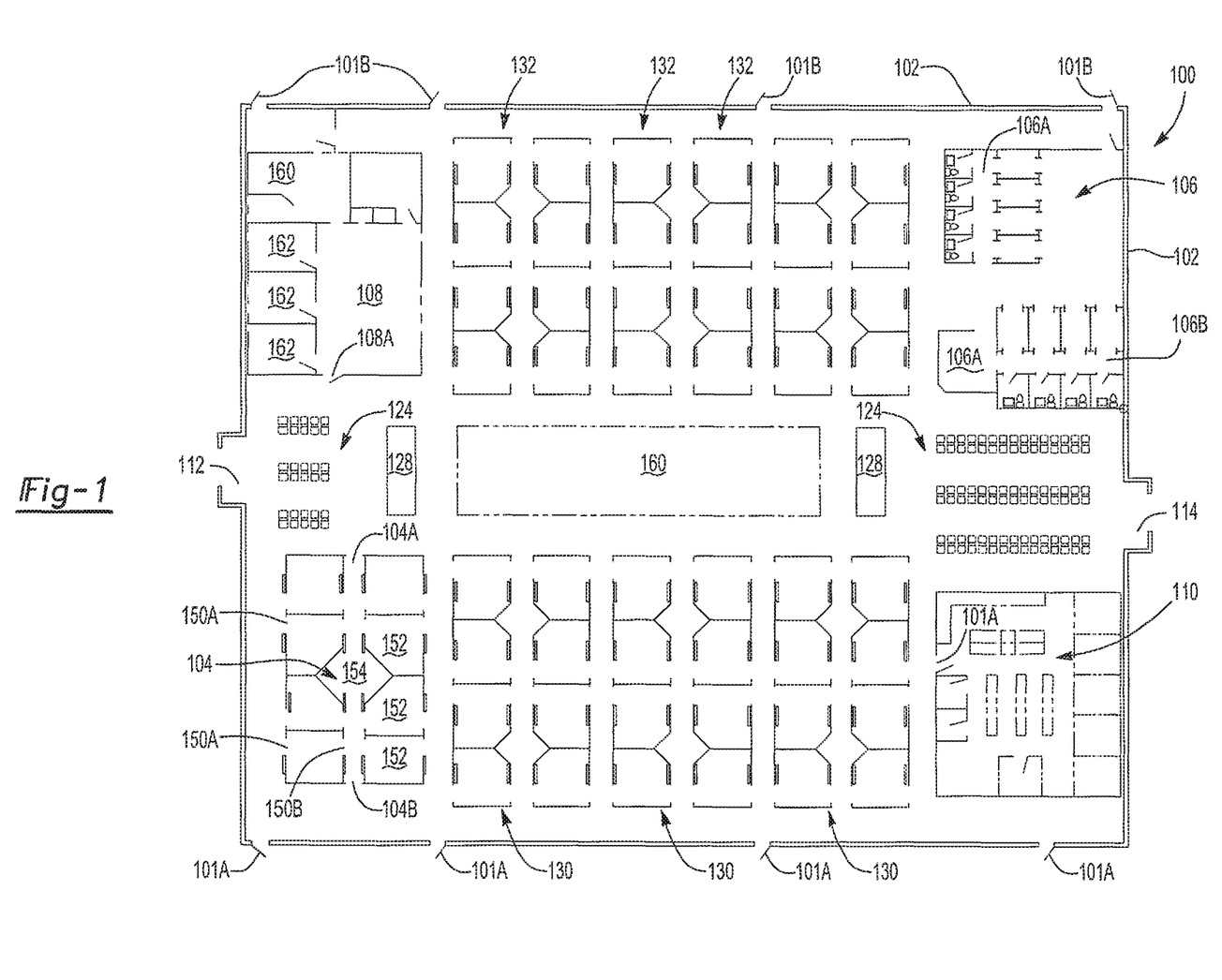
FIG. 1 depicts an exemplary elevational view of a first floor medical clinic layout of a building structure having waiting rooms, a lab, reception, primary care pods, specialist pods, pharmacy, urgent care, and imaging . . . etc. according to one or more embodiments shown and described herein.

Referring now to FIG. 1, the exemplary clinic layout 100 is generally rectangular or square in shape, having a main outer perimeter 102. The layout 100 includes a four corners design for ancillary components of this unique clinic design, with clinic space centralized between these components. This allows for more efficient coordination of multidisciplinary and multispecialty services and allows these services to be provided in one location, within a smaller footprint. The four corners include an urgent care space 104, a lab 106, an imaging center 108, and a pharmacy 110. The layout further includes two main entrances 112 and 114. The main entrances 112 and 114 include a waiting areas 124 and reception desks 128. Both main entrances 112 and 114 allow patients access to their desired service, either main clinic or ancillary services. This design provides patients with isolated and integrated care and utilizes unidirectional patient flow to increase healthcare delivery efficiency. The outer perimeter 102 of the layout 100 further includes exits 116, 118, 120, 122, which are configured to be exits only. In the present embodiment, the entrances 112, 114, are configured to be entrances only. The entrances and exits are stationed to be polar opposite sides of the structure, as located at 101A, 101B.

The urgent care space 104 includes an enclosed space set up similar to the primary care and specialty care pods. The urgent care space includes a center hallway 154 where care providers work. Patients are not permitted in the center hallway 154. A plurality of exam rooms 152 are positioned adjacent to the hallway 154. Each of the exam rooms 152 include two doors. One of the doors 150A is a dedicated door for patients. The other door 150B is a dedicated care provider door. Patients are not permitted to pass through the door 150B. This stricture The lab 106 includes a lab reception area 106A where patients check in. The lab is an area where care provides can collect and test samples from patients including urine, blood . . . etc. Areas 106A, 106B includes exam rooms and bathrooms for sample collection spaced apart by a hallway.

The imaging center 108 includes a plurality of rooms for x-ray and ultrasound as shown at 160, 162. The imaging center includes two doors 108A, 108B to facilitate patient flow through the imaging center.

The pharmacy 110 includes a door 110A located near both a side exit and a main entrance so as to facility patient flow through the pharmacy.

Figure 2:
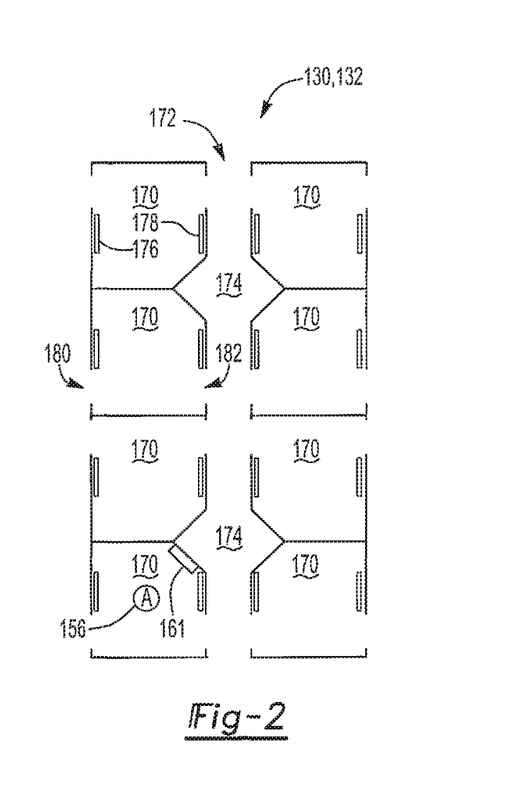
FIG. 2 depicts an exemplary set of pods (either primary care or specialist) according to one or more embodiments shown and described herein.

The layout 100 further includes a plurality of primary care pods 130 and specialist pods 132. Each of the pods 130, 132, as illustrated in FIG. 2, include a plurality of 8 exam rooms 170 each having a patient entrance/exit 180 and a care provider entrances/exit 182. The hallway 172 and the care provider space 174 is only accessible by the care providers, doctors, nurses . . . etc. The hallway 172 and the care provider space 174 shall not be accessible by any patients. The specific layout prevents unwanted interaction between care providers and patients by keeping the spaces that each party walks and moves separate. The patients go in and out of one door (180) and the care providers only go in and out of the other door (182). This specific layout prevents patients from overhearing care providers discussing the files and confidential information of other patients since only care providers are permitted in the hallway 172 and the care provider space 174. Each of the exam rooms 170 may further includes screen 161 and exam table 156.

It should be noted the layout 100 is nearly exemplary and not intended to limit the scope of the present invention. The layout 100 must comprise four corners and a plurality of pods, although the exact configuration, such as shown in FIG. 1, is not required and the specifics of each area may be adjusted in accordance with community needs.

Figure 3:
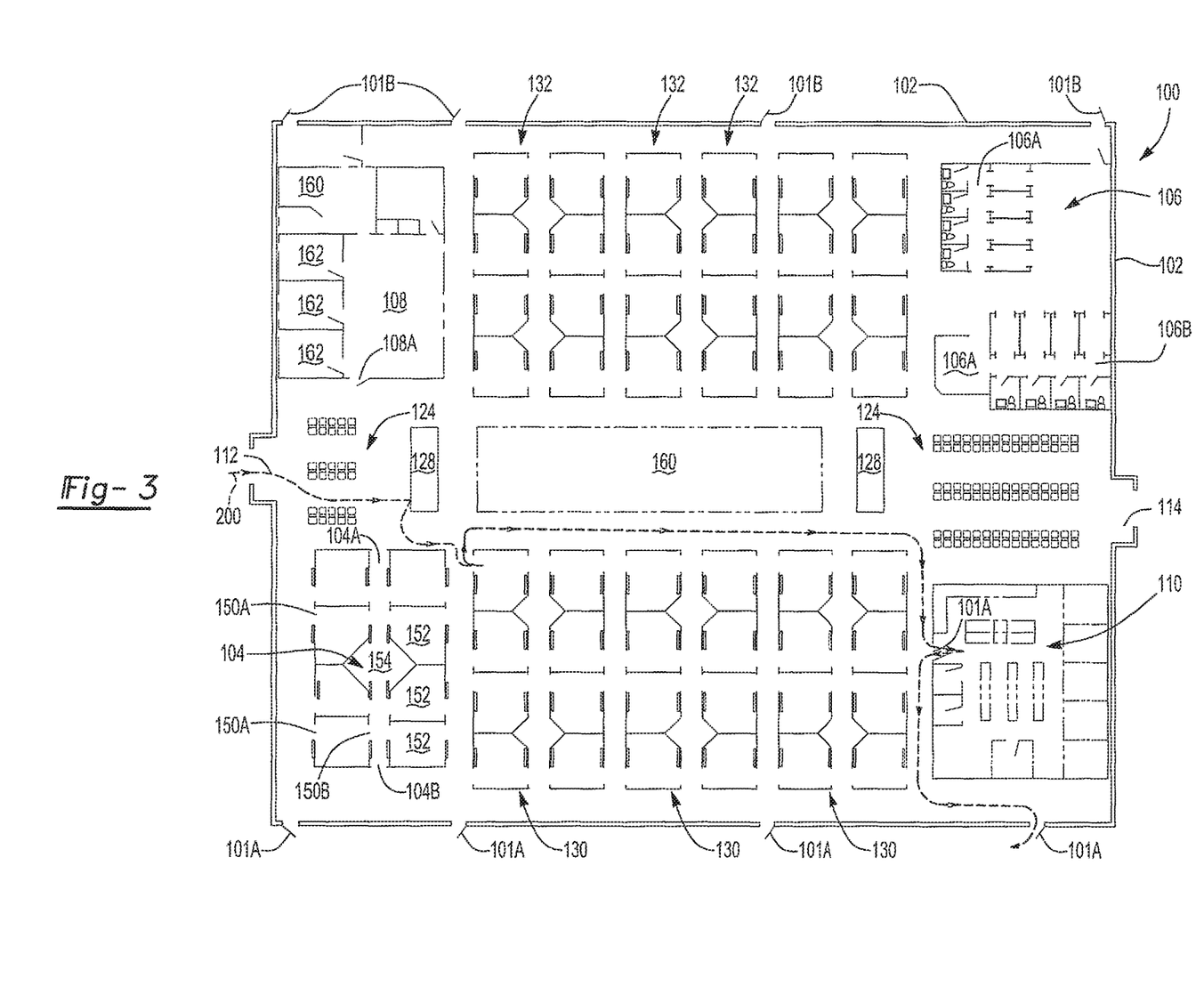
FIG. 3 depicts an exemplary elevational view of the building structure with illustrative flow arrows extending therethrough according to one or more embodiments shown and described herein.

FIGS. 3 through 7 illustrate exemplary paths taken by a patient when visiting the clinic 100. FIG. 3 depicts a patient path 200 wherein the patient enters the main entrance 112 and continues through the waiting area 124. After visiting reception 128 the patient moves to their designated primary care pod 130. The patient may then utilize the pharmacy 110 before exiting 122. Movement of the patient along the patient path 200 facilitates unidirectional patient flow through the clinic. The patient path 200 facilitates patient movement from the entrance 112 to one of the dedicated exits, in this embodiment, exit 101A, so as to increase clinic operational efficiency. This is further facilitated by the electronic standard adopted by the clinic, ensuring there is no need for patients to backtrack at any time.

Figure 4:
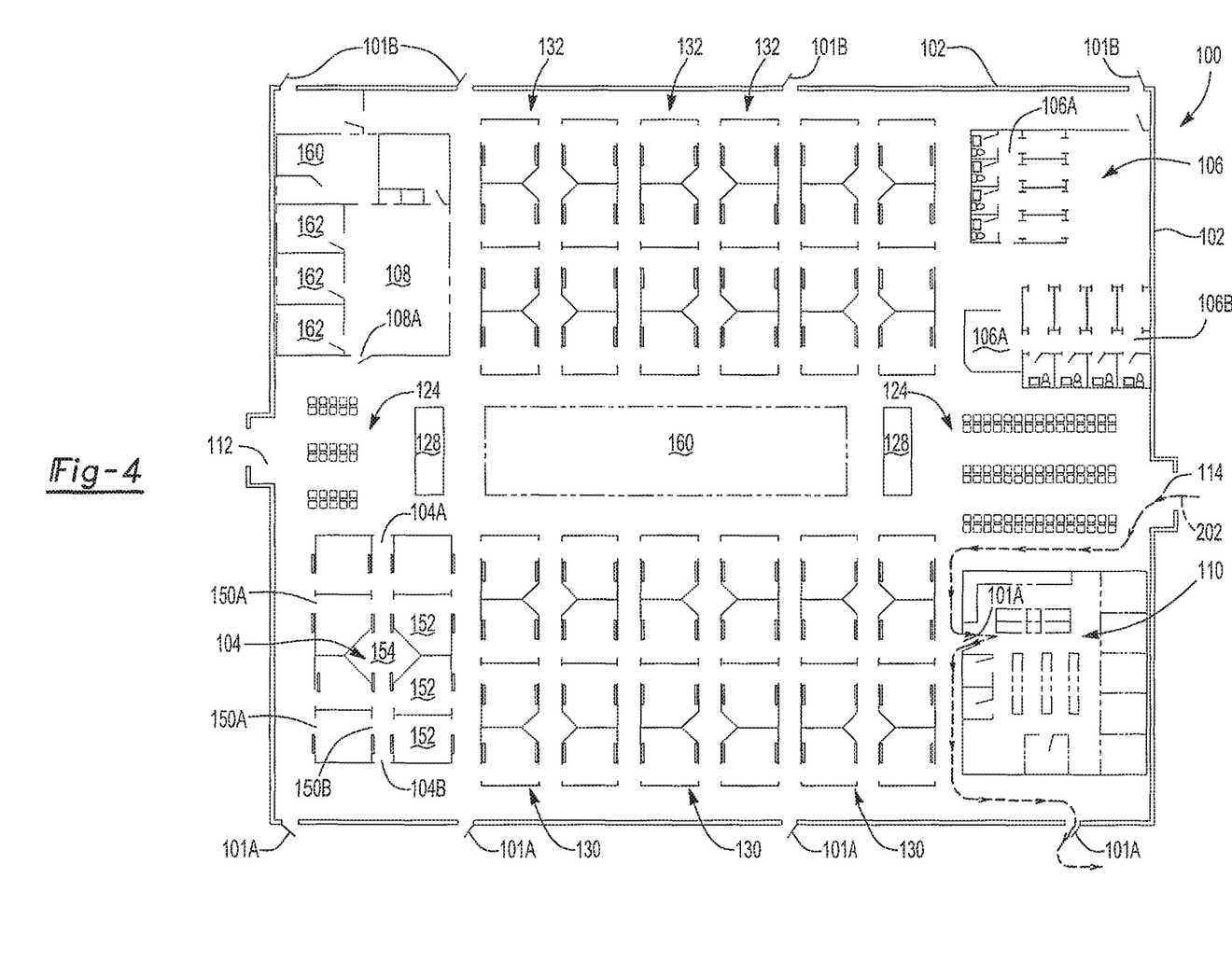
FIG. 4 depicts an exemplary building structure with illustrative flow arrows extending therethrough according to one or more embodiments shown and described herein.

FIG. 4 depicts an exemplary patient path 202 wherein the patient is only visiting the clinic to visit the pharmacy 110.

In this embodiment, the patient enters the main entrance 114 and visits the pharmacy 110 before exiting the dedicated exit 101A.

Figure 5:
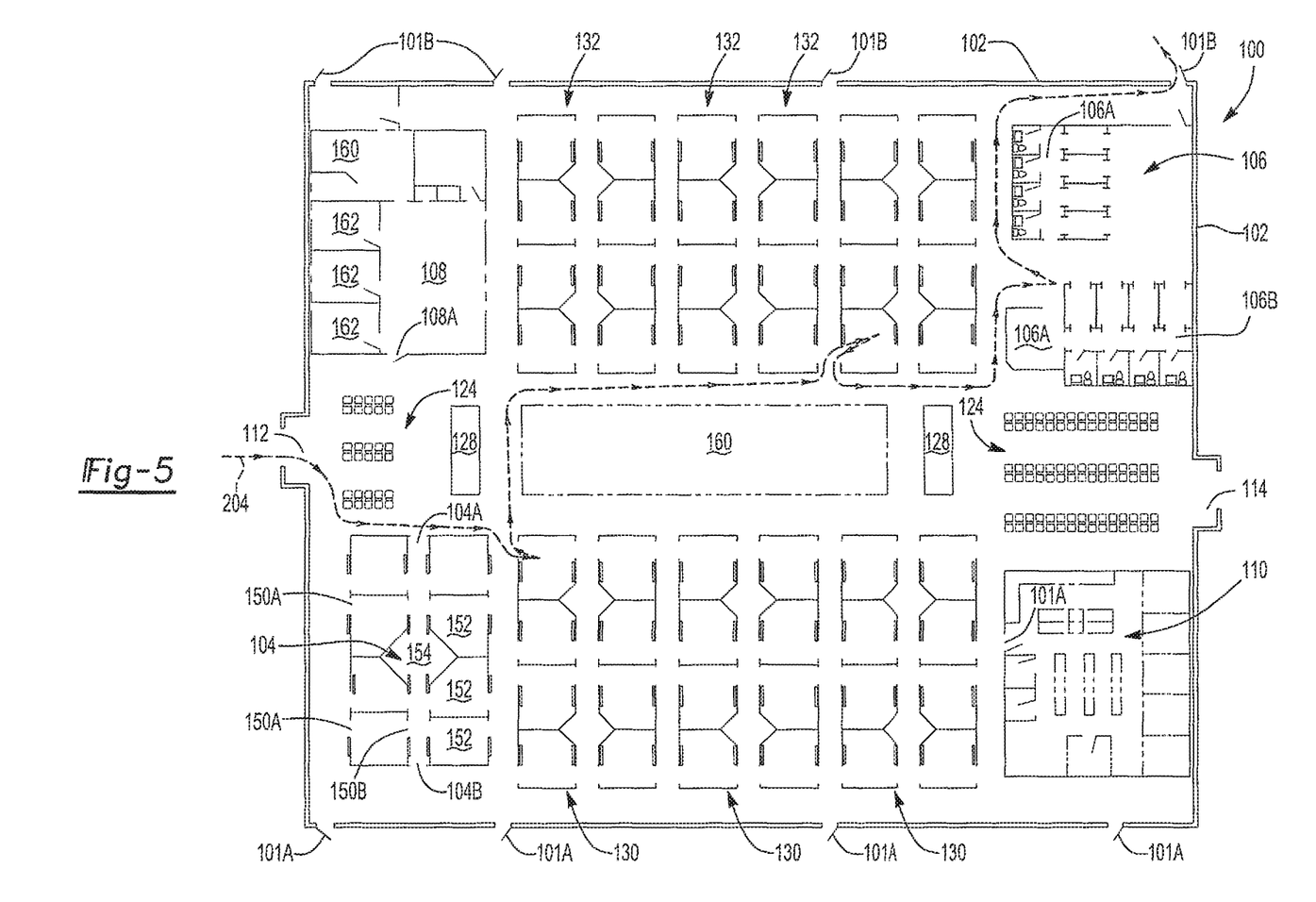
FIG. 5 depicts an exemplary building structure with illustrative flow arrows extending therethrough according to one or more embodiments shown and described herein.

Referring now to FIG. 5, a patient path 204 is provided wherein the patient enters the main entrance 112 into the waiting room 124. After visiting reception 128, the patient proceeds to a primary care pod 130. If needed, a specialist can be 'quick' consulted at, and will come to the patient's exam room, providing patient-centered care. In the route as shown in 204, the patient then visits the specialist 132 in the same visit. The patient may then proceed to the lab 106 before exiting the building 101B.

Figure 6:
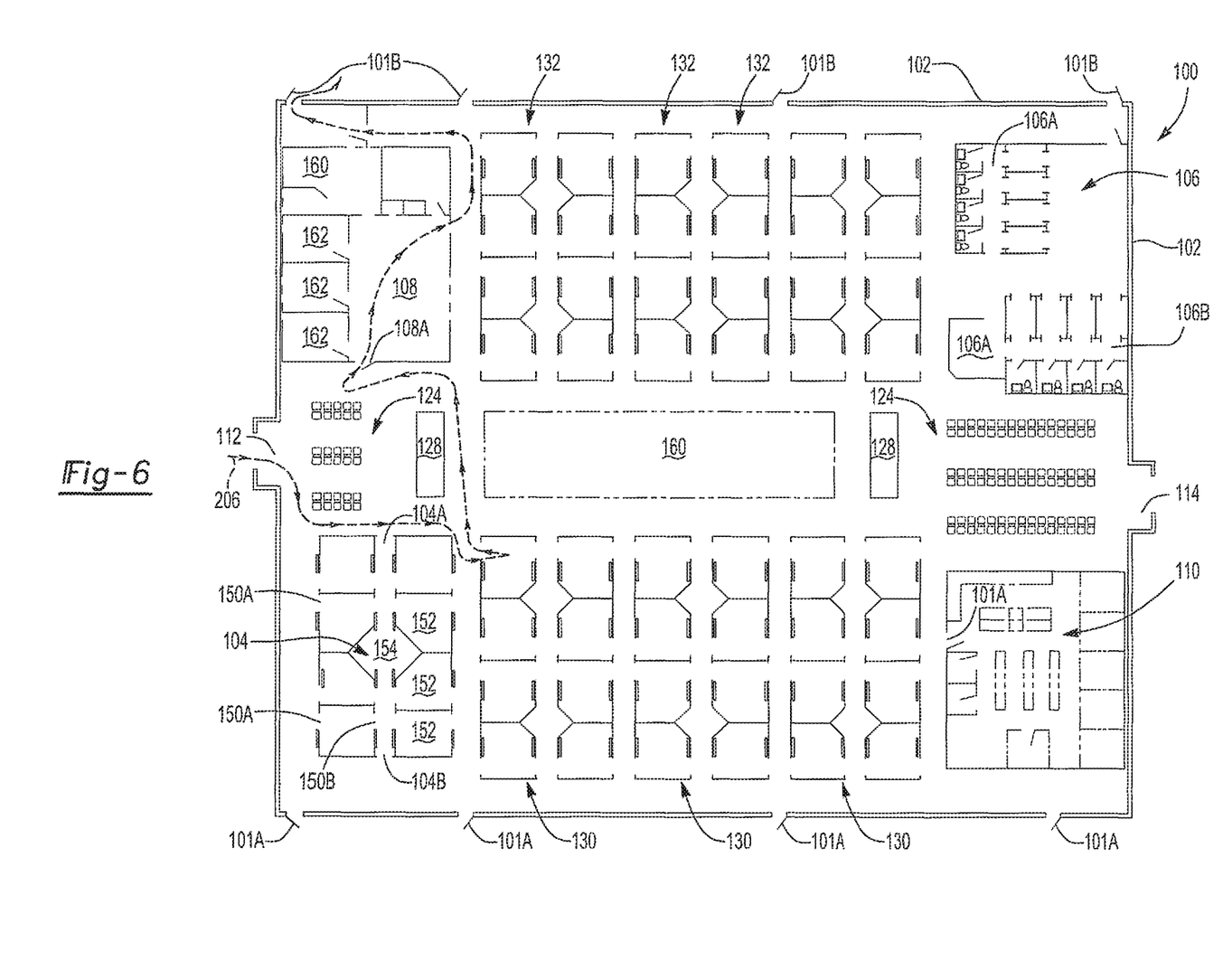
FIG. 6 depicts an exemplary building structure with illustrative flow arrows extending therethrough according to one or more embodiments shown and described herein.

FIG. 6 depicts a patient flow path 206 wherein the patient enters the clinic at the main entrance 112 and proceeds through the waiting room 124. After visiting reception 128 the patient proceeds to a primary care pod 130. The patient then visits the imaging center 108, and if needed, a specialist can be 'quick' consulted to see the patient in the imaging center, which will house additional pods, and patient exam rooms. The patient then exits the clinic at the dedicated exit 101B.

FIG. 6 further depicts the path of a doctor, or other care provider, at route 206A. This route show the path of a doctor moving between exam rooms 170 and through the hallway 172.

Figure 7:
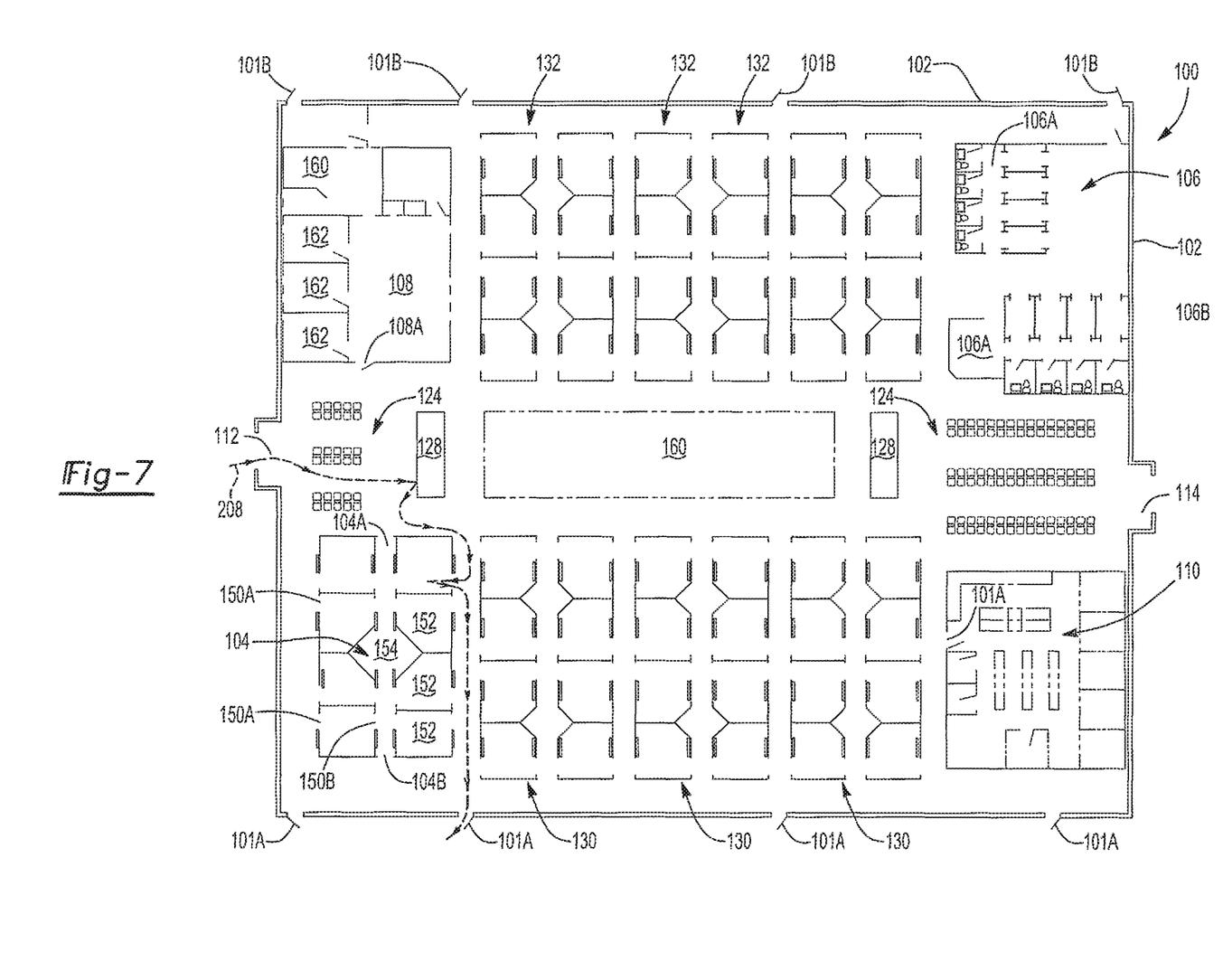
FIG. 7 depicts an exemplary building structure with illustrative flow arrows extending therethrough according to one or more embodiments shown and described herein.

Referring now to FIG. 7, a patient flow path 208 depicts wherein a patient enters the building through a main entrance 112 into the waiting room 124. After visiting reception 128, the patient may visit the urgent care 104 and exits the building through the dedicated exit 101A.

In some embodiments, a second and third floor may be provided on top of the first floor as illustrated in FIGS. 1 through 7. These additions can be added or omitted in a modular nature to suit geographical community needs. Similarly, a modular floor may be added for teaching, conference and private office use as needed. In order to provide adequate parking, while minimizing the facility's overall footprint, a parking garage will be available adjacent and connected to the main facility. The parking garage elevators will provide multi-floor access to the main facility. The second floor may include offices and a renal program/dialysis center accessible via the parking garage elevators.

It is noted that the terms "substantially" and "about" may be utilized herein to represent the inherent degree of uncertainty that may be attributed to any quantitative comparison, value, measurement, or other representation.

These terms are also utilized herein to represent the degree by which a quantitative representation may vary from a stated reference without resulting in a change in the basic function of the subject matter at issue.

While particular embodiments have been illustrated and described herein, it should be understood that various other changes and modifications may be made without departing from the spirit and scope of the claimed subject matter.

Moreover, although various aspects of the claimed subject matter have been described herein, such aspects need not be utilized in combination.

It is therefore intended that the appended claims cover all such changes and modifications that are within the scope of the claimed subject matter.

The invention claimed is:

1. A building structure housing a medical facility, the building structure contained within a rectangular configuration, the building structure comprising:

the building structure having two spaced apart exterior building entrances, the exterior building entrances positioned on a first set of opposed exterior walls, the first set of opposed exterior walls not including any exits, the exterior building entrances configured to be entrances only;

the building structure having at least two spaced apart exterior building exits, the exterior building exits positioned on a second set of opposed exterior walls, the second set of opposed exterior walls not including any entrances, the exterior building exits positioned on exterior walls separate from and perpendicular to said walls having said building entrances, the exists configured to be exists only;

an enclosed space defining a medical lab area positioned in one of the four corners of the building structure, the enclosed space defining the medical lab defined by two exterior walls;

an enclosed space defining a pharmacy area positioned in another of the four corners of the building structure, the enclosed space defining the pharmacy area defined by two exterior walls;

an enclosed space defining an urgent care area positioned in another of the four corners of the building structure, the enclosed space defining the urgent care area defined by two exterior walls;

an enclosed space defining an imaging area positioned in the last of the four corners of the building structure, the enclosed space defining the imaging area defined by two exterior walls;

each of the medical lab, the pharmacy, the urgent care, and the imaging areas spaced apart from each other; and a plurality of modular pods wherein each pod includes a plurality of patient exam rooms and a dedicated workspace with access hallways wherein at least one of the plurality of modular pods is configured for a general practice physician and at least one of the plurality of modular pods is configured to a specialist physician, the primary care physicians, specialists, pharmacist, and all clinic personnel work together within the same physical clinic space and operational model to provide a higher quality of healthcare to patients, each of the modular pods including the plurality of patient exam rooms and the dedicated works space all being self-contained, the entirety of the plurality of modular pods spaced apart from said exterior walls of the building structure, the dedicated first entrance/exit for patients positioned parallel with said exterior building entrances, the dedicated second entrance/exit for care providers positioned parallel with said exterior building exits.

2. The building structure of claim 1 wherein at least two pods are provided of said plurality of pods wherein at least one primary care pod and at least one specialty care pod are provided.

3. The building structure of claim 1 wherein the at least one primary care pod is spaced apart from the at least one specialty care pod.

4. The building structure of claim 1 wherein each of the plurality of pods includes a hallway spacing apart two sets of exam rooms.

* * * * *